(12) United States Patent  (10) Patent No.: US 8,362,244 B2
Takahashi et al.  (45) Date of Patent: Jan. 29, 2013

(54) METHOD FOR PRODUCING NUCLEOSIDE DERIVATIVES

(75) Inventors: Satoji Takahashi, Yokkaichi (JP);
Mitsuhiko Kojima, Yokkaichi (JP);
Shouichi Kondou, Yokkaichi (JP);
Tatsuya Ishikawa, Yokkaichi (JP);
Yoshinori Ogawa, Kawagoe (JP)

(73) Assignee: Ajinomoto Co., Inc., Tokyo (JP)

( * ) Notice: Subject to any disclaimer, the term of this patent is extended or adjusted under 35 U.S.C. 154(b) by 911 days.

(21) Appl. No.: 11/782,695

(22) Filed: Jul. 25, 2007

(65) Prior Publication Data

US 2007/0282104 A1 Dec. 6, 2007

Related U.S. Application Data

(63) Continuation of application No. PCT/JP2006/301096, filed on Jan. 25, 2006.

(30) Foreign Application Priority Data

Jan. 25, 2005 (JP) ................................ 2005-016596

(51) Int. Cl.
*C07D 473/34* (2006.01)
*C07D 473/30* (2006.01)
(52) U.S. Cl. ........................ 544/265; 544/277
(58) Field of Classification Search ................. 544/265, 544/277
See application file for complete search history.

(56) References Cited

U.S. PATENT DOCUMENTS

| | | | |
|---|---|---|---|
| 4,916,218 A | 4/1990 | Almond et al. | |
| 4,970,148 A | 11/1990 | Yokozeki et al. | |
| 5,290,927 A | 3/1994 | Honda et al. | |
| 5,310,895 A | 5/1994 | Shiragami et al. | |
| 5,466,793 A | 11/1995 | Honda et al. | |
| 5,480,851 A | 1/1996 | Tsurumi et al. | |
| 5,866,423 A * | 2/1999 | Sugawara et al. | 436/5 |
| 6,388,150 B1 | 5/2002 | Overbeek et al. | |
| 2003/0087873 A1* | 5/2003 | Stuyver et al. | 514/45 |

FOREIGN PATENT DOCUMENTS

| | | |
|---|---|---|
| JP | 63-185449 | 8/1988 |
| JP | 01-224390 | 9/1989 |
| JP | 02-117689 | 5/1990 |
| JP | 02-164895 | 6/1990 |
| JP | 02-291291 | 12/1990 |
| JP | 03-090096 | 4/1991 |
| JP | 03-190876 | 8/1991 |
| JP | 03-227997 | 10/1991 |
| JP | 05-219978 | 8/1993 |
| JP | 06-031181 | 2/1994 |
| JP | 11-513302 | 11/1999 |
| JP | 2002-535296 | 10/2002 |
| WO | WO97/12673 | 4/1997 |
| WO | WO 2006/080326 A1 | 8/2006 |

OTHER PUBLICATIONS

Brosette, Tetrahedron (2001), 57(38), 8129-8143.*
Mansuri, Journal of Organic Chemistry (1989), 54(20), 4780-5.*
Hiroshi Shiragami, et al.; "Synthesis of 2', 3'-Dideoxypurinenuceosides Via the Palladium Catalyzed Reduction of 9-(2,5-Di-O-Acetyl-3-Bromo-3-Deoxy-B-D-Xylofuranosyl) Purine Derivatives"; 1996; Nucleosides & Nucleotides, vol. 15, No. 1-3, pp. 31-45.
Morris J. Robins, et al.; "A Mild Conversion of Vicinal Diols to Alkenes. Efficient Transformation of Ribonucleosides Into 2' -Ene and 2',3' -Dideoxynucleosides 1"; 1984; Tetrahedron Letters, vol. 25, No. 4, pp. 367-370.

(Continued)

*Primary Examiner* — Mark Berch
(74) *Attorney, Agent, or Firm* — Oblon, Spivak, McClelland, Maier & Neustadt, L.L.P.

(57) ABSTRACT

The present invention relates to a method for producing a nucleoside derivative represented by formula (2), comprising the step of reducing a nucleoside of formula (1) in the presence of a noble metal catalyst comprising a carrier and a noble metal supported thereby, selected from the group consisting of (A) a homogeneously supported catalyst where the specific surface area of the noble metal is 95.0 m²/g or more and the particle size of the noble metal is 4.3 nm or less, and (B) a surface-loaded catalyst where the specific surface area of the noble metal is 56.0 m²/g or more and the particle size of the noble metal is 8.0 nm or less,

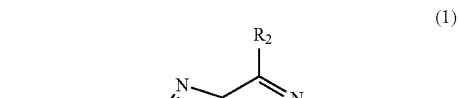

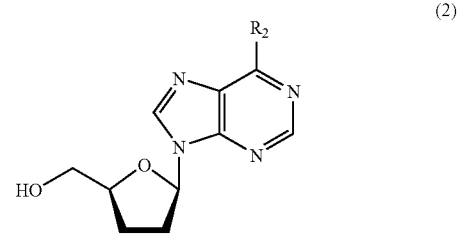

wherein $R_1$ is hydrogen or a protective group, $R_2$ is $NH_2$ or OH, $R_3$ is an acyl group, and X is a chlorine or bromine atom. According to the present invention, the yield can be made equal even when the amount of catalyst is smaller than that used for the conventional products.

15 Claims, No Drawings

OTHER PUBLICATIONS

John L. Dillon; "In Situ Activated Zinc-Copper Couple for the Preparation of a Key Intermediate in the Synthesis of Dideoxyinosine (DDI)"; 1997; Synthetic Communications, vol. 27, No. 24, pp. 4367-4371.

C.K. Chu, et al.; "General Syntheses of 2', 3'-Dideozynucleosides and 2', 3'-Didehydro-2', 3'-Dideoxynucleosides"; Apr. 28, 1989; The Journal of Organic Chemistry, vol. 54, No. 9, pp. 2217-2225.

Extended European Search Report issued Feb. 15, 2011, in European Application No. 06 71 2291.1, filed Jan. 25, 2006.

T. Hattori, et al., Stud. Surf. Sci. Catal., 31, 815-826 (1987).

Japanese Office Action mailed Mar. 5, 2012, in corresponding Japanese Patent Application No. 2007-500528 with English Translation (8 pp.).

Japanese Office Action dated Nov. 19, 2012 in corresponding Japanese Patent Application No. 2007-500528 with English Translation (4 pp.).

* cited by examiner

METHOD FOR PRODUCING NUCLEOSIDE DERIVATIVES

TECHNICAL FIELD

The present invention relates to methods for producing 2', 3'-dideoxyinosine useful as an antiviral agent, represented by the following formula (4), which is called didanosine (DDI) and hereinafter referred to as "DDI", and 2', 3'-dideoxyadenosine of the following formula (2)($R_2$ is $NH_2$), which is hereinafter referred to as "DDA", serving as an intermediate compound essential in producing the DDI.

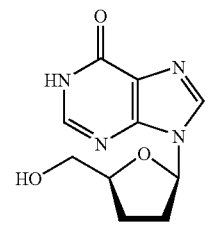
(4)

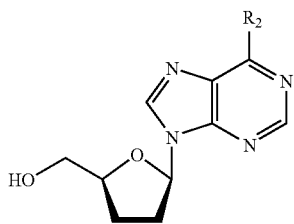
(2)

BACKGROUND OF THE INVENTION

The DDI is useful as an antiviral agent and has already been approved as an anti-AIDS drug in many countries including U.S.A., Japan and European countries.

To derive a didehydro (DD) compound from nucleoside, there is conventionally known, for example, a method where hydroxyl groups at the 2'- and 3'-positions of nucleoside are subjected to thiocarbonylation, followed by radical reduction to form a didehydrodideoxy (D4) derivative, and the D4 derivative is subjected to hydrogenation or the like, thereby obtaining a didehydro (DD) derivative (refer to Chu, C. K. et al. J. Org. Chem. 1989, 54, 2217-2225).

Reduction catalysts are used when the didehydro derivative is synthesized from nucleoside. Noble metal-supported catalysts can produce the target compounds in satisfactory yields. However, those catalysts themselves are so expensive that it was difficult to use those catalysts in large amounts.

Accordingly, there is an increasing demand for methods for producing the DDI and DDA in high yields at low cost.

DISCLOSURE OF INVENTION

Accordingly, an object of the present invention is to provide industrially advantageous methods for producing nucleoside derivatives, which can give equal yields even if the amount of catalyst used is smaller than that of the conventional catalysts.

After intensive researches and studies to solve the above-mentioned problem, it has been found that the DDA can be efficiently produced by using a particular noble metal catalyst even in a small amount. Namely, the present invention provides a method for producing a nucleoside derivative represented by

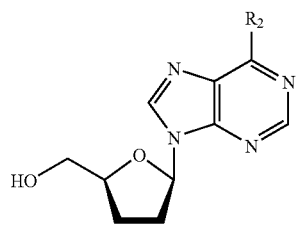
(2)

formula (2):
wherein $R_2$ is $NH_2$ or OH,
comprising the step of
reducing a nucleoside represented by the following formula (1):

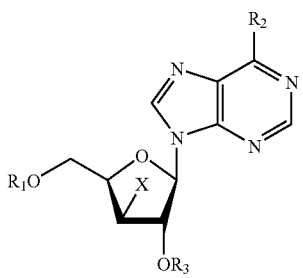
(1)

wherein $R_1$ is hydrogen or a protective group, $R_2$ is the same as that previously defined, $R_3$ is an acyl group, and X is a chlorine or bromine atom;
in the presence of a noble metal catalyst comprising a carrier and a noble metal supported thereby, selected from the group consisting of:
(A) a homogeneously supported catalyst where the specific surface area of the noble metal is 95.0 $m^2/g$ or more and the particle size of the noble metal is 4.3 nm or less, and
(B) a surface-loaded catalyst where the specific surface area of the noble metal is 56.0 $m^2/g$ or more and the particle size of the noble metal is 8.0 nm or less,
to obtain the nucleoside derivative represented by formula (2) above.

Also, the present invention provides a method for producing a nucleoside derivative represented by formula (2):

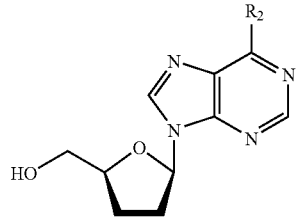
(2)

wherein $R_2$ is $NH_2$ or OH,
comprising the steps of:
converting a nucleoside represented by the following formula (1):

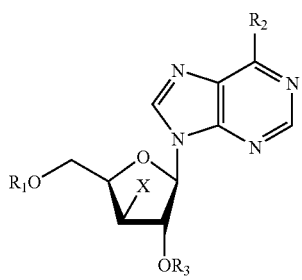

(1)

wherein $R_1$, $R_2$, $R_3$ and X are the same as those previously defined;
to a compound of formula (3):

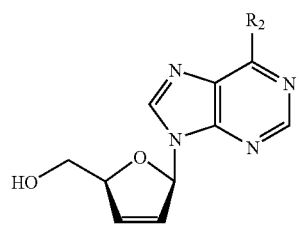

(3)

wherein $R_2$ is the same as that previously defined; and
reducing the thus obtained compound of formula (3) in the presence of a noble metal catalyst comprising a carrier and a noble metal supported thereby, selected from the group consisting of:

(A) a homogeneously supported catalyst where the specific surface area of the noble metal is 95.0 $m^2/g$ or more and the particle size of the noble metal is 4.3 nm or less, and (B) a surface-loaded catalyst where the specific surface area of the noble metal is 56.0 $m^2/g$ or more and the particle size of the noble metal is 8.0 nm or less, to obtain the nucleoside derivative represented by formula (2) above.

Furthermore, the present invention provides a method for producing 2',3'-dideoxyinosine represented by the following formula (4):

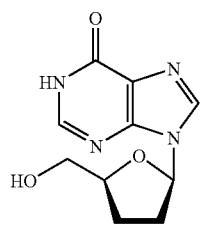

(4)

comprising the step of reacting the nucleoside derivative of formula (2) obtainable from the method of the present invention with an enzyme to cause deamination.

EFFECTS OF THE INVENTION

According to the present invention, even if the amount of catalyst is smaller, the yields of DDA and DDI can be made equal to those of the methods that use conventional catalysts. Also, the methods of the present invention can produce DDA and DDI in shorter periods of reaction time even though the amount of catalyst is made smaller than that used to produce the conventional products. Furthermore, according to the present invention, generation of the impurities which are especially difficult to be removed by the process of purification after the reduction reaction can be controlled, so that the amounts of impurities contained in the resultant DDA and DDI can be decreased. In principle, therefore, further purification processes such as chromatography and the like are not necessary before the products are subjected to the subsequent step. Namely, DDA and DDI can be obtained by more convenient procedures. The catalyst used in the present invention can be collected within a short time, which can enhance the productivity.

BEST MODE FOR CARRYING OUT THE INVENTION

In the first aspect, the present invention provides a method for producing a nucleoside derivative represented by the above-mentioned formula (2) comprising the step of reducing the nucleoside of formula (1) using a particular noble metal catalyst as previously mentioned.

According to the second aspect of the present invention, there is provided a method for producing a nucleoside derivative represented by the above-mentioned formula (2) comprising the steps of converting the nucleoside of formula (1) to a compound of formula (3), and thereafter reducing the compound using a particular noble metal catalyst as previously mentioned.

Specific examples of the protective group herein used include acyl group, substituted or unsubstituted benzyl group, silyl group, benzhydryl group, trityl group and the like. Examples of the substituents for the benzyl group include alkyl groups having 1 to 12 carbon atoms such as methyl group, ethyl group, n-propyl group, i-propyl group and the like; cycloalkyl groups having 3 to 12 carbon atoms such as cyclopropyl group, cyclobutyl group, cyclopentyl group, cyclohexyl group and the like; alkoxyl groups having 1 to 12 carbon atoms such as methoxy group, ethoxy group, n-propoxy group, i-propoxy group and the like; acyloxy groups having 2 to 12 carbon atoms such as acetoxy group, benzoyloxy group and the like; hydroxyl group; halogen atoms such as fluorine, chlorine, bromine, iodine and the like; vinyl group; allyl group; aryl groups such as phenyl group, naphthyl group, furyl group, indolyl group, pyridyl group and the like; carbonyl groups such as formyl group, acetyl group, trifluoroacetyl group, benzoyl group, methoxycarbonyl group and the like; sulfonyl groups such as alkylsulfonyl group, arylsulfonyl group, sulfonamide and the like; amino group; primary amino groups such as N-methylamino group, N-ethylamino group, N-n-propylamino group, N-isopropylamino group and the like; secondary amino groups such as N,N-dimethylamino group, N,N-diethylamino group, and the like; nitro group; nitroso group; cyano group; and haloalkyl groups such as monofluoromethyl group, difluoromethyl group, trifluoromethyl group, monochloromethyl group, dichloromethyl group, trichloromethyl group, pentafluoroethyl group and the like. The alkoxyl groups having 1 to 12 carbon atoms are preferable as the substituent.

The acyl groups herein used include acetyl group, propionyl group, butyryl group and the like.

In the present invention, $R_1$ preferably represents a protective group, more preferably an acyl group, and further preferably acetyl group. $R_2$ may preferably be $NH_2$, and $R_3$ may preferably represent acetyl group.

More specifically, as the nucleoside represented by formula (1) used for the production method of the present invention, preferably used are 9-(2,5-O-diacetyl-3-bromo-3-deoxy-β-D-xylofuranosyl)adenine wherein $R_1$ is acetyl group, $R_2$ is $NH_2$, $R_3$ is acetyl group, and X is a bromine atom; 9-(2,5-O-diacetyl-3-bromo-3-deoxy-β-D-xylofuranosyl)hypoxanthine wherein $R_1$ is acetyl group, $R_2$ is OH, $R_3$ is acetyl group, and X is a bromine atom; and the like.

The nucleoside of the above-mentioned formula (1) used in the production method of the present invention can be prepared according to the conventional method, for example, as described in Japanese Patent Unexamined Publication (JP Kokai) Hei 3-227997. To be more specific, adenosine is first suspended in acetic acid and trimethyl ortho-acetate is added to the suspension. The obtained mixture is stirred at a predetermined temperature for a predetermined period of time, and thereafter methanol is distilled away under reduced pressure. The resultant compound is gradually added to a mixture of acetic acid and acetyl bromide, followed by stirring at a predetermined temperature, whereby the nucleoside of formula (1) is prepared.

The reducing catalyst for use in the present invention is a noble metal catalyst comprising a carrier and a noble metal supported by the carrier, selected from the group consisting of (A) and (B) shown below:

(A) a homogeneously supported catalyst where the specific surface area of the noble metal is 95.0 $m^2/g$ or more and the particle size of the noble metal is 4.3 nm or less, and (B) a surface-loaded catalyst where the specific surface area of the noble metal is 56.0 $m^2/g$ or more and the particle size of the noble metal is 8.0 nm or less.

The term "homogeneously supported catalyst" herein used means a catalyst where the catalytic components are homogeneously distributed throughout the inside of the carrier. On the other hand, the term "surface-loaded catalyst" means a catalyst where the catalytic components are mostly spread on the surface portion of the carrier. The methods for producing those catalysts are not particularly limited, but impregnation is commonly employed. For example, the carrier is suspended in water, and to the obtained suspension is added a noble metal containing compound in such an amount that corresponds to the predetermined loading of noble metal, to cause the noble metal containing compound to be adsorbed by the carrier. After that, the mixture is subjected to reduction and then dried. To control the distribution of the catalytic components, competitive adsorption can be used although there is no particular limitation on the method. More specifically, it is possible to intentionally make either the homogeneously supported catalyst or the surface-loaded catalyst by adding an organic acid or inorganic acid to the noble metal containing compound under the control of the amount to be added, pH value, impregnation time, surface area and pore size of the carrier, and the like.

Such a homogeneously supported palladium catalyst and a surface-loaded palladium catalyst can be produced by the above-mentioned method. Alternatively, commercially available catalysts having a predetermined specific surface area and palladium distribution, for example, a homogeneously supported 10% palladium on carbon catalyst (made by Kawaken Fine Chemicals Co., Ltd.) and a surface-loaded 10% palladium on carbon catalyst (made by Kawaken Fine Chemicals Co., Ltd.) can be used as they are.

With respect to the catalyst (A) used in the present invention, homogeneously supported catalysts where the specific surface area of the noble metal is 115.0 $m^2/g$ or more and the particle size of the noble metal is 3.5 nm or less are preferred. The use of such homogeneously supported catalysts is advantageous because the reduction can be completed in a short period of time and the reduction reaction can be carried out efficiently even when the amount of catalyst is small.

In the case of the catalyst (B) for use in the present invention, surface-loaded catalysts where the specific surface area of the noble metal is 65.0 $m^2/g$ or more and the particle size of the noble metal is 7.5 nm or less are preferred. By use of such surface-loaded catalysts, the reduction can favorably be completed in a short period of time and the reduction reaction can be caused even though the amount of catalyst is decreased.

More preferably, the degree of dispersion of noble metal may be 21.5% or more in the homogeneously supported catalyst (A), and 15.0% or more in the surface-loaded catalyst (B). When those catalysts are used, the reduction can advantageously be completed in a shorter period of time and a smaller amount of catalyst is enough to cause the reduction reaction.

The catalysts (A) and (B) may be dry or contain water.

Most preferable homogeneously supported catalyst is the one where the specific surface area of the noble metal is 120.0 $m^2/g$ or more and the particle size of the noble metal is 3.5 nm or less. Particularly preferable is that having a noble metal dispersion degree of 25.0% or more.

Most preferable surface-loaded catalyst is the one where the specific surface area of the noble metal is 70.0 $m^2/g$ or more and the particle size of the noble metal is 6.0 nm or less. The use of such catalysts is advantageous because the reduction reaction can be completed in a very short period of time even when the amount of catalyst is decreased. Particularly preferable is that having a noble metal dispersion degree of 15.5% or more.

The specific surface area of noble metal, the particle size of noble metal, and the dispersion degree of noble metal in the catalyst used in the present invention can be determined by the CO gas adsorption method. Using a fully automatic equipment for measuring gas adsorption on catalyst (Model R-6015, made by Ohkura Riken Inc.), the CO gas adsorption is determined by the pulse method after pretreatment by hydrogen reduction.

The specific surface area of noble metal, the particle size of noble metal, and the dispersion degree of noble metal in the catalyst can be increased or decreased appropriately by controlling the production conditions of the catalyst. More specifically, the control becomes possible by replacing the kind of carrier and changing the impregnation conditions.

The noble metals for constituting the catalyst used in the present invention include palladium, platinum, ruthenium, rhodium, iridium and the like. Of those, palladium and platinum are preferable, and in particular palladium is most preferable. The catalyst used in the present invention may further comprise alkali metals or the like, such as sodium, potassium, lithium and so on, in addition to the noble metal.

According to the present invention, any carriers can be used for the catalyst as long as they are inactive under the reaction conditions. For example, there can be employed activated carbon, silica, α-alumina, γ-alumina, silica-alumina, and a variety of metal oxides and composite oxides and the like. In particular, activated carbon is most preferable.

The loading of noble metal supported by the catalyst used in the present invention is preferably between 1 to 25%, on a basis of noble metal atom, and more preferably between 5 to 15%, based on the weight of the carrier particles.

When the loading of noble metal is within the above-mentioned range, the catalyst can be prepared conveniently, and produced efficiently.

The catalyst for use in the present invention can be repeatedly used. When the catalyst is reused, the catalyst may be collected by subjecting a reaction liquid to filtration after completion of the reduction reaction, and the catalyst thus collected is ready to be reused as it is or after dried under reduced pressure. If dried, the drying may preferably be carried out at 105° C. for 2 hours. The recycled catalyst may be used alone or in combination with unused fresh catalyst for the reduction reaction. In the latter case, the recycled catalyst may be mixed with the unused catalyst at any ratio.

In the first aspect, when the reduction reaction is caused using only the unused fresh catalyst, the amount of the catalyst on a basis of noble metal atom may preferably be 0.001 equivalent or more, and more preferably 0.005 equivalent or more, with respect to the nucleoside of formula (1). When the catalyst is used in the above-mentioned amount ratio, the reaction can be completed in a short period of time and therefore the efficient production can be attained. When the recycled catalyst and fresh catalyst are used together for the reduction reaction, two kinds of catalysts may be combined together at any ratio. In this case, the fresh catalyst may be used or not. Preferably, the reduction reaction may be carried out at atmospheric pressure and at a reaction temperature ranging from room temperature to 40° C., more preferably from room temperature to 30° C., within 50 hours, more preferably within 20 hours. As the reaction solvent, there can be employed a mixed solvent of acetonitrile and water, a mixed solvent of water and an ester solvent such as ethyl acetate, and the like. In particular, a mixed solvent of acetonitrile and water and a mixed solvent of water and ethyl acetate are preferable. The reaction is preferably caused under basic conditions. To make the reaction solvent basic, the conventional basic substances such as sodium hydroxide and the like can be used as a reagent. The reaction solvent may preferably be adjusted to pH8 or more, more preferably pH8 or more and pH11 or less, and further preferably pH8.5 or more and pH10.5 or less. The reduction reaction can be carried out, for example, by blowing hydrogen into a reaction vessel of 50 ml or more. The amount of hydrogen to be introduced may preferably be 2 equivalent or more with respect to the nucleoside represented by formula (1).

In the second aspect, the nucleoside of formula (1) can be converted to a compound of formula (3) by the reaction in the presence of zinc powder, zinc-copper complex or the like. It is preferable to use the zinc powder, zinc-copper complex or the like in 2 to 3 equivalent on a basis of the concentration of metal element. Examples of the reaction solvent include dimethylformamide (DMF), acetonitrile, methanol, ethanol, THF and the like. In particular, DMF, acetonitrile and methanol are preferred. The reaction may preferably be carried out under neutral or basic conditions. To make the reaction solvent neutral or basic, the conventional basic substances such as sodium hydroxide and the like can be used as a reagent. The reaction solvent may preferably be adjusted to pH7 or more, and more preferably pH7 or more and pH11 or less. In the second aspect, the nucleoside derivative of formula (1) can be obtained by reducing the compound of formula (3) in the same manner as in the first aspect mentioned above.

According to the present invention, after completion of the reduction reaction, the reaction liquid may be subjected to filtration, if necessary, to remove the catalyst, or to saponification by the addition of a basic aqueous solution, for example, an aqueous solution of sodium hydroxide. The process of saponification can isolate the target nucleoside derivative of formula (2) at higher purity. According to the present invention, the nucleoside derivative of formula (2) can be obtained in a yield of 80% or more.

Furthermore, DDI of formula (4) can be prepared from the nucleoside derivatives represented by formula (2) obtainable from the method of the present invention by enzymatic deamination in accordance with the conventional method, for example, as described in Japanese Patent Unexamined Publication (JP Kokai) Hei 2-291291. The enzyme that can be used in this case includes deaminase and the like. Particularly, adenosine deaminase is preferable. Alternatively, cultured bacterial cells capable of generating such an enzyme may be used. The reaction can preferably be caused at a temperature ranging from 5 to 70° C., more preferably 20 to 60° C. under atmospheric pressure, within 10 minutes to 10 days. The reaction system may preferably be adjusted to pH3 to 10, more preferably pH4 to 9. As the reaction proceeds, the pH is increased by the generation of ammonia. Therefore, in order to achieve better results, the increase in the pH may be controlled by using an acid. Examples of the acid include mineral acids such as hydrochloric acid, phosphoric acid, sulfuric acid, nitric acid and the like; and organic acids such as formic acid, acetic acid, citric acid and the like. According to the present invention, the DDI represented by formula (4) can be obtained in a yield of 70% or more.

The present invention will now be explained more specifically with reference to the following Examples, which are given for illustration of the invention and are not intended to be limiting thereof.

EXAMPLES

Examples and Comparative Examples Employed the Following Catalysts:

Catalyst (A): 10% palladium on carbon catalyst (Wet), made by Kawaken Fine Chemicals Co., Ltd. (a homogeneously supported type catalyst where the specific surface area of the noble metal is 120 $m^2/g$, the particle size of the noble metal is 3.5 nm, and the dispersion degree of the noble metal is 27.0%)

Catalyst (B): 10% palladium on carbon catalyst (Wet), made by Kawaken Fine Chemicals Co., Ltd. (a surface-loaded type catalyst where the specific surface area of the noble metal is 104 $m^2/g$, the particle size of the noble metal is 4.0 nm, and the dispersion degree of the noble metal is 23.3%)

Catalyst (C): 10% palladium on carbon catalyst (Wet), made by Kawaken Fine Chemicals Co., Ltd. (a homogeneously supported type catalyst where the specific surface area of the noble metal is 67 $m^2/g$, the particle size of the noble metal is 6.2 nm, and the dispersion degree of the noble metal is 15.1%)

Catalyst (D): 10% palladium on carbon catalyst (Wet), made by Kawaken Fine Chemicals Co., Ltd. (a homogeneously supported type catalyst where the specific surface area of the noble metal is 81 $m^2/g$, the particle size of the noble metal is 5.2 nm, and the dispersion degree of the noble metal is 18.1%)

Example 1

After 368 g of a mixed solution of acetonitrile and water containing 19.4 wt % of 9-(2,5-O-diacetyl-3-bromo-3-deoxy-β-D-xylofuranosyl)adenine (71.4 g, 172 mmol) was poured into a 500-ml eggplant-shaped flask, the solution was adjusted to the pH range of 8.5 to 10.5 by the addition of aqueous sodium hydroxide solution. Thereafter, the catalyst (A) was added in an amount of 10.9 g (0.028 equivalent on a basis of palladium atom) and hydrogen was blown into the reaction system to carry out a reduction reaction, with the reaction system being maintained under basic condition by use of aqueous sodium hydroxide solution. The reduction reaction was completed in 5.5 hours.

After completion of the reduction, the reaction liquid was subjected to filtration to remove the catalyst, and thereafter subjected to saponification by the addition of aqueous sodium hydroxide solution. According to the quantitative analysis by HPLC, 2',3'-dideoxyadenosine was found to be obtained in a yield of 80%. Further, 0.4% of 2',3'-didehydroxy-2',3'-epoxyadenosine was included as impurities.

Example 2

9-(2,5-O-diacetyl-3-bromo-3-deoxy-β-D-xylofuranosyl)adenine was subjected to the reduction reaction in the same manner as in Example 1 except that the catalyst (B) was used in an amount of 10.0 g (0.028 equivalent on a basis of palladium atom). The reduction reaction was completed in 4.5 hours.

After completion of the reduction, the reaction liquid was subjected to filtration to remove the catalyst, and thereafter subjected to saponification by the addition of aqueous sodium hydroxide solution. According to the quantitative analysis by HPLC, 2',3'-dideoxyadenosine was found to be obtained in a yield of 84%.

Further, 0.4% of 2',3'-didehydroxy-2',3'-epoxyadenosine was included as impurities.

Comparative Example 1

9-(2,5-O-diacetyl-3-bromo-3-deoxy-β-D-xylofuranosyl)adenine was subjected to the reduction reaction in the same manner as in Example 1 except that the catalyst (C) was used in an amount of 4.7 g (0.03 equivalent on a basis of palladium atom). The reduction reaction was completed in 9 hours.

After completion of the reduction, the reaction liquid was subjected to filtration to remove the catalyst, and thereafter subjected to saponification by the addition of aqueous sodium hydroxide solution. According to the quantitative analysis by HPLC, 2',3'-dideoxyadenosine was found to be obtained in a yield of 77%.

Further, 2.4% of 2',3'-didehydroxy-2',3'-epoxyadenosine was included as impurities.

Comparative Example 2

9-(2,5-O-diacetyl-3-bromo-3-deoxy-β-D-xylofuranosyl)adenine was subjected to the reduction reaction in the same manner as in Example 1 except that the catalyst (D) was used in an amount of 11.1 g (0.028 equivalent on a basis of palladium atom). The reduction reaction was completed in 8.0 hours.

After completion of the reduction, the reaction liquid was subjected to filtration to remove the catalyst, and thereafter subjected to saponification by the addition of aqueous sodium hydroxide solution. According to the quantitative analysis by HPLC, 2',3'-dideoxyadenosine was found to be obtained in a yield of 78%.

Further, 0.6% of 2',3'-didehydroxy-2',3'-epoxyadenosine was included as impurities.

Example 3

368 g of a mixed solution of acetonitrile and water containing 19.4 wt % of 9-(2,5-O-diacetyl-3-bromo-3-deoxy-β-D-xylofuranosyl)adenine (71.3 g, 172 mmol) was subjected to a reduction reaction in the same manner as in Example 1 except that the catalyst (A) once used in the reduction reaction by the same procedure as in Example 1 and thereafter dried under reduced pressure was used in an amount of 6.4 g (0.028 equivalent on a basis of palladium atom). The reduction reaction was completed in 11.5 hours.

After completion of the reduction, the reaction liquid was subjected to filtration to remove the catalyst, and thereafter subjected to saponification by the addition of aqueous sodium hydroxide solution. According to the quantitative analysis by HPLC, 2',3'-dideoxyadenosine was found to be obtained in a yield of 81%.

Example 4

9-(2,5-O-diacetyl-3-bromo-3-deoxy-β-D-xylofuranosyl)adenine was subjected to a reduction reaction in the same manner as in Example 2 except that the catalyst (B) once used in the reduction reaction by the same procedure as in Example 2 and thereafter dried under reduced pressure was used in an amount of 6.7 g (0.028 equivalent on a basis of palladium atom). The reduction reaction was completed in 7 hours.

After completion of the reduction, the reaction liquid was subjected to filtration to remove the catalyst, and thereafter subjected to saponification by the addition of aqueous sodium hydroxide solution. According to the quantitative analysis by HPLC, 2',3'-dideoxyadenosine was found to be obtained in a yield of 82%.

Comparative Example 3

9-(2,5-O-diacetyl-3-bromo-3-deoxy-β-D-xylofuranosyl)adenine was subjected to a reduction reaction in the same manner as in Comparative Example 1 except that the catalyst (C) once used in the reduction reaction by the same procedure as in Comparative Example 1 and thereafter dried under reduced pressure was used in an amount of 6.7 g (0.028 equivalent on a basis of palladium atom). The reduction reaction was completed in 15.5 hours.

After completion of the reduction, the reaction liquid was subjected to filtration to remove the catalyst, and thereafter subjected to saponification by the addition of aqueous sodium hydroxide solution. According to the quantitative analysis by HPLC, 2',3'-dideoxyadenosine was found to be obtained in a yield of 75%.

Comparative Example 4

9-(2,5-O-diacetyl-3-bromo-3-deoxy-β-D-xylofuranosyl)adenine was subjected to a reduction reaction in the same manner as in Comparative Example 2 except that the catalyst (D) once used in the reduction reaction by the same procedure as in Comparative Example 2 and thereafter dried under reduced pressure was used in an amount of 11.0 g (0.028 equivalent on a basis of palladium atom). The reduction reaction was completed in 11.5 hours.

After completion of the reduction, the reaction liquid was subjected to filtration to remove the catalyst, and thereafter subjected to saponification by the addition of aqueous sodium hydroxide solution. According to the quantitative analysis by HPLC, 2',3'-dideoxyadenosine was found to be obtained in a yield of 62%.

Example 5

After 368 g of a mixed solution of acetonitrile and water containing 19.4 wt % of 9-(2,5-O-diacetyl-3-bromo-3- deoxy-β-D-xylofuranosyl)adenine (71.3 g, 172 mmol) was poured into a 500-ml eggplant-shaped flask, the solution was adjusted to the pH range of 8.5 to 10.5 by the addition of aqueous sodium hydroxide solution. Thereafter, 1.65 g of the fresh catalyst (B) (0.0046 equivalent on a basis of palladium atom) and 26.6 g of the wet catalyst (B) obtained just after collected without the drying process were added and hydrogen was blown into the reaction system to carry out a reduction reaction, with the reaction system being maintained under basic condition by use of aqueous sodium hydroxide solution. The reduction reaction was completed in 3.8 hours.

After completion of the reduction, the reaction liquid was subjected to filtration to collect 33.4 g of the catalyst. It took 0.5 hours to take out the catalyst by filtration. Apart of the filtrate was subjected to saponification by the addition of aqueous sodium hydroxide solution. According to the quantitative analysis by HPLC, 2',3'-dideoxyadenosine was found to be obtained in a yield of 83%.

The remaining filtrate was concentrated and subjected to saponification by the addition of aqueous sodium hydroxide solution. Through the steps of extraction and crystallization, 29.4 g of 2',3'-dideoxyadenosine was obtained in a yield of 66% as wet crystals (not dried). Furthermore, the obtained crystals were subjected to enzymatic deamination, whereby 2',3'-dideoxyinosine was obtained.

Comparative Example 5

368 g of a mixed solution of acetonitrile and water containing 19.4 wt % of 9-(2,5-O-diacetyl-3-bromo-3-deoxy-β-D-xylofuranosyl)adenine (71.3 g, 172 mmol) was adjusted to the pH range of 8.5 to 10.5 by the addition of aqueous sodium hydroxide solution. Thereafter, 5.12 g of the fresh catalyst (C) (0.013 equivalent on a basis of palladium atom) and 18.6 g of the wet catalyst (C) obtained just after collected without the drying process were added and hydrogen was blown into the reaction system to carry out a reduction reaction, with the reaction system being maintained under basic condition by use of aqueous sodium hydroxide solution. The reduction reaction was completed in 10.5 hours.

After completion of the reduction, the reaction liquid was subjected to filtration to collect 28.1 g of the catalyst. It took 1.5 hours to take out the catalyst by filtration. The filtrate was subjected to saponification by the addition of aqueous sodium hydroxide solution. According to the quantitative analysis by HPLC, 2',3'-dideoxyadenosine was found to be obtained in a yield of 78%.

The invention claimed is:

1. A method for producing a nucleoside derivative of formula (2):

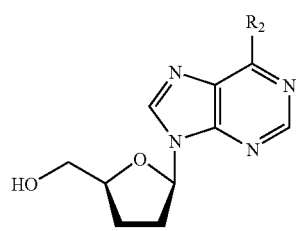

(2)

wherein $R_2$ is $NH_2$ or OH,
comprising
reducing a nucleoside of formula (1):

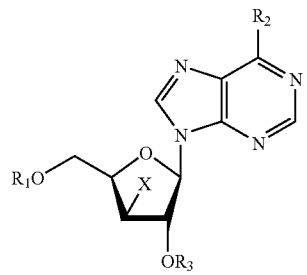

(1)

wherein $R_1$ is hydrogen or a protective group, $R_2$ is $NH_2$ or OH, $R_3$ is an acyl group, and X is a chlorine or bromine atom,
in the presence of a noble metal catalyst comprising a carrier and a noble metal supported thereby, selected from the group consisting of:
(A) a homogeneously supported catalyst where the specific surface area of the noble metal as determined by the CO gas adsorption method is 95.0 m$^2$/g or more and the particle size of the noble metal is 4.3 nm or less, and
(B) a surface-loaded catalyst where the specific surface area of the noble metal as determined by the CO gas adsorption method is 56.0 m$^2$/g or more and the particle size of the noble metal is 8.0 nm or less,
to obtain the nucleoside derivative of formula (2).

2. A method for producing a nucleoside derivative of formula (2):

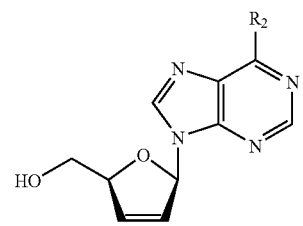

(3)

wherein $R_2$ is $NH_2$ or OH,
comprising:
converting a nucleoside of formula (1):

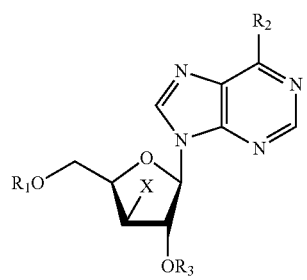

(1)

wherein $R_1$ is hydrogen or a protective group, $R_2$ is $NH_2$ or OH, $R_3$ is an acyl group, and X is a chlorine or bromine atom;

to a compound of formula (3):

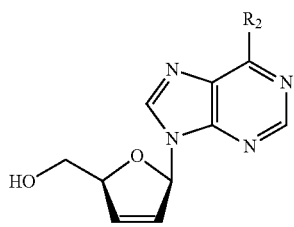

(3)

wherein $R_2$ is $NH_2$ or OH; and reducing the obtained compound of formula (3) in the presence of a noble metal catalyst comprising a carrier and a noble metal supported thereby, selected from the group consisting of:

(A) a homogeneously supported catalyst where the specific surface area of the noble metal as determined by the CO gas adsorption method is 95.0 $m^2/g$ or more and the particle size of the noble metal is 4.3 nm or less, and (B) a surface-loaded catalyst where the specific surface area of the noble metal as determined by the CO gas adsorption method is 56.0 $m^2/g$ or more and the particle size of the noble metal is 8.0 nm or less, to obtain the nucleoside derivative of formula (2).

3. The method of claim 1, wherein the catalyst (A) is a homogeneously supported catalyst where the specific surface area of the noble metal as determined by the CO gas adsorption method is 115.0 $m^2/g$ or more and the particle size of the noble metal is 3.5 nm or less, and the catalyst (B) is a surface-loaded catalyst where the specific surface area of the noble metal as determined by the CO gas adsorption method is 65.0 $m^2/g$ or more and the particle size of the noble metal is 7.5 nm or less.

4. The method of claim 2, wherein the catalyst (A) is a homogeneously supported catalyst where the specific surface area of the noble metal as determined by the CO gas adsorption method is 115.0 $m^2/g$ or more and the particle size of the noble metal is 3.5 nm or less, and the catalyst (B) is a surface-loaded catalyst where the specific surface area of the noble metal as determined by the CO gas adsorption method is 65.0 $m^2/g$ or more and the particle size of the noble metal is 7.5 nm or less.

5. The method of claim 1, wherein the catalyst (A) is a homogeneously supported catalyst where the dispersion degree of the noble metal is 21.5% or more, and the catalyst (B) is a surface-loaded catalyst where the dispersion degree of the noble metal is 15.0% or more.

6. The method of claim 2, wherein the catalyst (A) is a homogeneously supported catalyst where the dispersion degree of the noble metal is 21.5% or more, and the catalyst (B) is a surface-loaded catalyst where the dispersion degree of the noble metal is 15.0% or more.

7. A method for producing 2',3'-dideoxyinosine of formula (4):

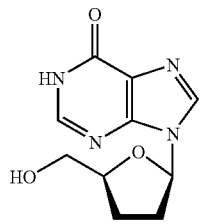

(4)

comprising:
reducing a nucleoside of formula (1):

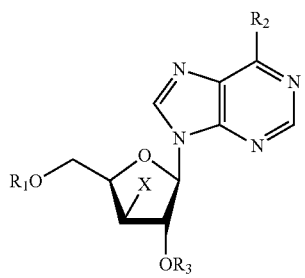

(1)

wherein $R_1$ is hydrogen or a protective group, $R_2$ is $NH_2$, $R_3$ is an acyl group, $R_3$ is an acyl group, and X is a chlorine or bromine atom, in the presence of a noble metal catalyst comprising a carrier and a noble metal supported thereby, selected from the group consisting of:

(A) a homogeneously supported catalyst where the specific surface area of the noble metal as determined by the CO gas adsorption method is 95.0 $m^2/g$ or more and the particle size of the noble metal is 4.3 nm or less, and (B) a surface-loaded catalyst where the specific surface area of the noble metal as determined by the CO gas adsorption method is 56.0 $m^2/g$ or more and the particle size of the noble metal is 8.0 nm or less, to obtain the nucleoside derivative of formula (2):

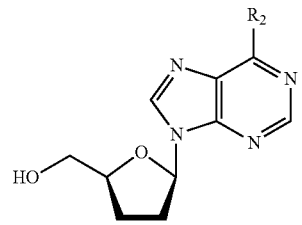

(2)

wherein $R_2$ is $NH_2$, and
reacting the nucleoside derivative of formula (2) thus obtained with an enzyme to cause deamination.

8. The method of claim 1, wherein the nucleoside of formula (1) is 9-(2,5-O-diacetyl-3-bromo-3-deoxy-β-D-xylofuranosyl) adenine or 9-(2,5-O-diacetyl-3-bromo-3-deoxy-β-D-xylofuranosyl)hypoxanthine.

9. The method of claim 2, wherein the nucleoside of formula (1) is 9-(2,5-O-diacetyl-3-bromo-3-deoxy-β-D-xylofuranosyl) adenine or 9-(2,5-O-diacetyl-3-bromo-3-deoxy-β-D-xylofuranosyl)hypoxanthine.

10. The method of claim 1, wherein the catalyst (A) is a homogeneously supported catalyst where the specific surface area of the noble metal as determined by the CO gas adsorption method is 120.0 m$^2$/g or more and the particle size of the noble metal is 3.5 nm or less, and the catalyst (B) is a surface-loaded catalyst where the specific surface area of the noble metal as determined by the CO gas adsorption method is 70.0 m$^2$/g or more and the particle size of the noble metal is 6.0 nm or less.

11. The method of claim 2, wherein the catalyst (A) is a homogeneously supported catalyst where the specific surface area of the noble metal as determined by the CO gas adsorption method is 120.0 m$^2$/g or more and the particle size of the noble metal is 3.5 nm or less, and the catalyst (B) is a surface-loaded catalyst where the specific surface area of the noble metal as determined by the CO gas adsorption method is 70.0 m$^2$/g or more and the particle size of the noble metal is 6.0 nm or less.

12. The method of claim 10, wherein the catalyst (A) has a dispersion degree of noble metal of 25.0% or more, and the catalyst (B) has a dispersion degree of noble metal of 15.5% or more.

13. The method of claim 11, wherein the catalyst (A) has a dispersion degree of noble metal of 25.0% or more, and the catalyst (B) has a dispersion degree of noble metal of 15.5% or more.

14. The method of claim 1, wherein the noble metal contained in the catalyst (A) or (B) is palladium or platinum, and the carrier for the catalyst (A) or (B) is activated carbon.

15. The method of claim 2, wherein the noble metal contained in the catalyst (A) or (B) is palladium or platinum, and the carrier for the catalyst (A) or (B) is activated carbon.

\* \* \* \* \*